United States Patent
Weinberg

(10) Patent No.: US 11,141,398 B2
(45) Date of Patent: Oct. 12, 2021

(54) METHODS FOR DECREASING INJURIES ASSOCIATED WITH INTRAOPERATIVE HYPOTENSION

(71) Applicant: ResQ Pharma, Inc., Chicago, IL (US)

(72) Inventor: Guy Weinberg, Chicago, IL (US)

(73) Assignee: The United States Government as Represented by the Department of Veterans Affairs, Washington, DC (US)

( * ) Notice: Subject to any disclaimer, the term of this patent is extended or adjusted under 35 U.S.C. 154(b) by 0 days.

(21) Appl. No.: 16/476,404

(22) PCT Filed: Jan. 5, 2018

(86) PCT No.: PCT/US2018/012623
§ 371 (c)(1),
(2) Date: Jul. 8, 2019

(87) PCT Pub. No.: WO2018/129345
PCT Pub. Date: Jul. 12, 2018

(65) Prior Publication Data
US 2020/0046668 A1 Feb. 13, 2020

Related U.S. Application Data

(60) Provisional application No. 62/443,755, filed on Jan. 8, 2017.

(51) Int. Cl.
| | | |
|---|---|---|
| A61K 9/00 | (2006.01) |
| A61K 9/107 | (2006.01) |
| A61P 9/00 | (2006.01) |
| A61K 31/201 | (2006.01) |
| A61K 31/202 | (2006.01) |
| A61K 38/08 | (2019.01) |

(52) U.S. Cl.
CPC .......... *A61K 31/201* (2013.01); *A61K 31/202* (2013.01); *A61K 38/085* (2013.01); *A61K 9/0019* (2013.01); *A61K 9/107* (2013.01); *A61P 9/00* (2018.01)

(58) Field of Classification Search
CPC .................................................. A61K 9/0019
See application file for complete search history.

(56) References Cited

U.S. PATENT DOCUMENTS

| | | | | |
|---|---|---|---|---|
| 2006/0166182 A1* | 7/2006 | Weinberg | ............ | A01N 1/0226 435/1.1 |
| 2012/0095095 A1* | 4/2012 | Deckelbaum | .......... | A61K 31/22 514/547 |
| 2015/0335664 A1* | 11/2015 | Ho | ...................... | A61K 31/661 514/77 |

FOREIGN PATENT DOCUMENTS

WO  2017083780 A1  5/2017

OTHER PUBLICATIONS

Pubmed Abstract of Shan-ling Liu et al. "Protective effect of intralipid on myocardial ischemia/reperfusion injury in isolated rat heart." vol. 20(4), originally published Apr. 2008. Obtained from https://pubmed.ncbi.nlm.nih.gov/18419958/ on Jul. 20, 2020. (Year: 2008).*

J Li et al. "Intralipid, a Clinically Safe Compound, Protects the Heart Against Ischemia-Reperfusion Injury More Efficiently Than Cyclosporine-A." Anesthesiology, vol. 117 No. 4, Oct. 2012, pp. 836-846. (Year: 2012).*

BCH Tsui et al. "Use of Intralipid in managing refractory hypotension following epidural blockade." Canadian Journal of Anesthesiology, vol. 62, 2015, pp. 548-549. (Year: 2015).*

Judith A. R. van Waes, Wilton A. van Klei, M.D, Duminda N. Wijeysundera, Leo van Wolfswinkel, Thomas F. Lindsay, W. Scott Beattie. "Association between Intraoperative Hypotension and Myocardial Injury after Vascular Surgery." Anesthesiology, vol. 124(1), 2016, pp. 35-44. (Year: 2016).*

Michael Walsh, Philip J. Devereaux, Amit X. Garg, Andrea Kurz, Alparslan Turan, Reitze N. Rodseth, Jacek Cywinski, Lehana Thabane, Daniel I. Sessler. "Relationship between Intraoperative Mean Arterial Pressure and Clinical Outcomes after Noncardiac Surgery." Anesthesiology, vol. 19(3), pp. 507-515. (Year: 2013).*

Ferrante Santos Gragasin. "Anesthesia and the Aging Vasculature: Effects of Propofol on Hemodynamics and Vascular Function." PhD Thesis, University of Alberta, Spring 2014, pp. 1-220 and 19 unnumbered page (239 total sheets). (Year: 2014).*

Extended European Search Report for related EP Application No. 18736737 dated Sep. 28, 2020, 9 pages.

* cited by examiner

*Primary Examiner* — Isaac Shomer

(74) *Attorney, Agent, or Firm* — Polsinelli PC

(57) ABSTRACT

The present disclosures provides methods for decreasing injuries associated with intraoperative hypotension by intravenously administering to a subject a therapeutically effective amount of a fat emulsion, following a period of intraoperative hypotension and after the subject's mean arterial blood pressure has recovered. The disclosure also provides methods for preventing injuries associated with intraoperative hypotension, particularly for surgical candidates that have an increased risk for intraoperative hypotension. Non-limiting examples of injuries contemplated herein include myocardial injury, myocardial infarction, and acute kidney injury.

4 Claims, No Drawings

METHODS FOR DECREASING INJURIES ASSOCIATED WITH INTRAOPERATIVE HYPOTENSION

CROSS REFERENCE TO RELATED APPLICATIONS

This application claims the benefit of U.S. provisional application No. 62/443,755, filed Jan. 8, 2017, which is hereby incorporated by reference in its entirety.

FIELD OF THE INVENTION

The present disclosure provides methods for decreasing injuries associated with intraoperative hypotension by intravenously administering to a subject a therapeutically effective amount of a fat emulsion following a period of intraoperative hypotension and after the subject's mean arterial blood pressure has recovered. The disclosure also provides methods for preventing injuries associated with intraoperative hypotension, particularly for surgical candidates that have an increased risk for intraoperative hypotension. Non-limiting examples of injuries contemplated herein include myocardial injury, myocardial infarction, and acute kidney injury.

BACKGROUND OF THE INVENTION

Various degrees of hypotension are common during surgery, and it has been suggested that intraoperative hypotension contributes to organ injury. Consistent with this theory, hypotension, defined in various ways, is weakly associated with acute kidney injury and strongly associated with myocardial infarction and death. See, for example, Salmasi et al., *Anesthesiology* 2017, 126:47-65. To reduce the risk of acute kidney injury and myocardial injury, Salmasi et al. propose maintaining an intraoperative mean arterial pressure (MAP) greater than 65 mmHg. In reality, though, it is not always possible to maintain intraoperative MAP at 66 mmHg or greater. Accordingly, there remains a need in the art for methods to decrease the risk of injuries associated with intraoperative MAP less than 66 mmHg.

SUMMARY OF INVENTION

In an aspect, the present disclosure encompasses a method for preventing myocardial injury in a subject who will undergo surgery, optionally a subject with an increased risk for intraoperative hypotension, the method comprising intravenously administering to the subject, before surgery begins, a therapeutically effective amount of a fat emulsion. The prevention can result in at least a 10% decrease in myocardial injury as compared to a control group that did not receive the fat emulsion before surgery. In certain embodiments, the intraoperative hypotension occurred for at least about 30 seconds, at least about one minute, at least about five minutes, or at least about ten minutes and the subject's arterial blood flow was reduced but not completely occluded during the period of intraoperative hypotension; and optionally the fat emulsion is Intralipid® 20% and the dosage of Intralipid® 20% is about 10 mL to about 100 mL.

In another aspect, the present disclosure encompasses a method for preventing acute kidney injury in a subject who will undergo surgery, optionally a subject with an increased risk for intraoperative hypotension, the method comprising intravenously administering to the subject, before surgery begins, a therapeutically effective amount of a fat emulsion. The prevention can result in at least a 10% decrease in acute kidney injury as compared to a control group that did not receive the fat emulsion before surgery. In certain embodiments, the intraoperative hypotension occurred for at least about 30 seconds, at least about one minute, at least about five minutes, or at least about ten minutes and the subject's arterial blood flow was reduced but not completely occluded during the period of intraoperative hypotension; and optionally the fat emulsion is Intralipid® 20% and the dosage of Intralipid® 20% is about 10 mL to about 100 mL.

In another aspect, the present disclosure encompasses a method for preventing postoperative myocardial infarction in a subject who will undergo surgery, optionally a subject with an increased risk for intraoperative hypotension, the method comprising intravenously administering to the subject, before surgery begins, a therapeutically effective amount of a fat emulsion. The prevention can result in at least a 10% decrease in postoperative myocardial infarction as compared to a control group that did not receive the fat emulsion before surgery. In certain embodiments, the intraoperative hypotension occurred for at least about 30 seconds, at least about one minute, at least about five minutes, or at least about ten minutes and the subject's arterial blood flow was reduced but not completely occluded during the period of intraoperative hypotension; and optionally the fat emulsion is Intralipid® 20% and the dosage of Intralipid® 20% is about 10 mL to about 100 mL.

In another aspect, the present disclosure encompasses a method for decreasing postoperative mortality in a subject who will undergo surgery, optionally a subject with an increased risk for intraoperative hypotension, the method comprising intravenously administering to the subject, before surgery begins, a therapeutically effective amount of a fat emulsion, wherein mortality is reduced by at least 10% as compared to a control group that did not receive the fat emulsion. In certain embodiments, the intraoperative hypotension occurred for at least about 30 seconds, at least about one minute, at least about five minutes, or at least about ten minutes and the subject's arterial blood flow was reduced but not completely occluded during the period of intraoperative hypotension; and optionally the fat emulsion is Intralipid® 20% and the dosage of Intralipid® 20% is about 10 mL to about 100 mL.

In another aspect, the present disclosure encompasses a method for decreasing myocardial injury in a subject following intraoperative hypotension, optionally a subject who had an increased risk for intraoperative hypotension prior to surgery, the method comprising intravenously administering to the subject a therapeutically effective amount of a fat emulsion after the subject's mean arterial pressure (MAP) is recovered to greater than or equal to 66 mmHg, wherein administration of the therapeutically effective amount of the fat emulsion results in at least a 10% decrease in a marker of myocardial injury (e.g., cardiac troponin, heart-type fatty acid binding protein, etc.) as compared to a control group that did not receive the fat emulsion. In certain embodiments, the intraoperative hypotension occurred for at least about 30 seconds, at least about one minute, at least about five minutes, or at least about ten minutes and the subject's arterial blood flow was reduced but not completely occluded during the period of intraoperative hypotension. In certain embodiments, the intraoperative hypotension occurred for at least about 30 seconds, at least about one minute, at least about five minutes, or at least about ten minutes and the subject's arterial blood flow was reduced but not completely occluded during the period of intraoperative hypotension. In certain embodiments, the intraoperative hypotension occurred for at least about 30 seconds, at least about one minute, at least about five minutes, or at least about ten minutes and the subject's arterial blood flow was reduced but not completely occluded during the period of intraoperative hypotension; and optionally the fat emulsion is Intralipid® 20% and the dosage of Intralipid® 20% is about 10 mL to about 100 mL.

In another aspect, the present disclosure encompasses a method for decreasing acute kidney injury in a subject following intraoperative hypotension, optionally a subject who had an increased risk for intraoperative hypotension prior to surgery, the method comprising intravenously administering to the subject a therapeutically effective amount of a fat emulsion after the subject's mean arterial pressure (MAP) is recovered to greater than or equal to 66 mmHg, wherein administration of the therapeutically effective amount of the fat emulsion results in at least a 10% decrease in a marker of acute kidney injury (e.g., creatinine, lipocalin-2, etc.) as compared to a control group that did not receive the fat emulsion. In certain embodiments, the intraoperative hypotension occurred for at least about 30 seconds, at least about one minute, at least about five minutes, or at least about ten minutes and the subject's arterial blood flow was reduced but not completely occluded during the period of intraoperative hypotension; and optionally the fat emulsion is Intralipid® 20% and the dosage of Intralipid® 20% is about 10 mL to about 100 mL.

In another aspect, the present disclosure encompasses a method for decreasing postoperative myocardial infarction in a subject following intraoperative hypotension, optionally a subject who had an increased risk for intraoperative hypotension prior to surgery, the method comprising intravenously administering to the subject a therapeutically effective amount of a fat emulsion after the subject's mean arterial pressure (MAP) is recovered to greater than or equal to 66 mmHg, wherein administration of the therapeutically effective amount of the fat emulsion results in at least a 10% decrease in a postoperative myocardial infarction as compared to a control group that did not receive the fat emulsion. In certain embodiments, the intraoperative hypotension occurred for at least about 30 seconds, at least about one minute, at least about five minutes, or at least about ten minutes and the subject's arterial blood flow was reduced but not completely occluded during the period of intraoperative hypotension; and optionally the fat emulsion is Intralipid® 20% and the dosage of Intralipid® 20% is about 10 mL to about 100 mL.

In another aspect, the present disclosure encompasses a method for decreasing postoperative mortality in a subject following intraoperative hypotension, optionally a subject who had an increased risk for intraoperative hypotension prior to surgery, the method comprising intravenously administering to the subject a therapeutically effective amount of a fat emulsion after the subject's mean arterial pressure (MAP) is recovered to greater than or equal to 66 mmHg, wherein mortality reduced by at least 10% as compared to a control group that did not receive the fat emulsion. In certain embodiments, the intraoperative hypotension occurred for at least about 30 seconds, at least about one minute, at least about five minutes, or at least about ten minutes and the subject's arterial blood flow was reduced but not completely occluded during the period of intraoperative hypotension; and optionally the fat emulsion is Intralipid® 20% and the dosage of Intralipid® 20% is about 10 mL to about 100 mL.

In another aspect, the present disclosure encompasses a method for treating ischemic reperfusion injury in a subject in a non-shock state, optionally a subject who had an increased risk for intraoperative hypotension prior to surgery, the method comprising intravenously administering to a subject a therapeutically effective amount of a fat emulsion after the subject has received one or more reperfusion therapies to restore mean arterial pressure to 66 mmHg or higher, wherein the subject is not in shock at the time the fat emulsion is administered. In certain embodiments, the intraoperative hypotension occurred for at least about 30 seconds, at least about one minute, at least about five minutes, or at least about ten minutes and the subject's arterial blood flow was reduced but not completely occluded during the period of intraoperative hypotension; and optionally the fat emulsion is Intralipid® 20% and the dosage of Intralipid® 20% is about 10 mL to about 100 mL.

In another aspect, the present disclosure encompasses a method for decreasing 1-year mortality for a subject whose has intraoperative hypotension while under general anesthesia, optionally a subject who had an increased risk for intraoperative hypotension prior to surgery, the method comprising intravenously administering to the subject a therapeutically effective amount of a fat emulsion after the subject has received one or more reperfusion therapies to restore mean arterial pressure to 66 mmHg or higher, wherein the subject is not in shock at the time the fat emulsion is administered. In certain embodiments, the intraoperative hypotension occurred for at least about 30 seconds, at least about one minute, at least about five minutes, or at least about ten minutes and the subject's arterial blood flow was reduced but not completely occluded during the period of intraoperative hypotension; and optionally the fat emulsion is Intralipid® 20% and the dosage of Intralipid® 20% is about 10 mL to about 100 mL.

In another aspect, the present disclosure encompasses a method for decreasing 3-year mortality for a subject whose has intraoperative hypotension while under general anesthesia, optionally a subject who had an increased risk for intraoperative hypotension prior to surgery, the method comprising intravenously administering to the subject a therapeutically effective amount of a fat emulsion after the subject has received one or more reperfusion therapies to restore mean arterial pressure to 66 mmHg or higher, wherein the subject is not in shock at the time the fat emulsion is administered. In certain embodiments, the intraoperative hypotension occurred for at least about 30 seconds, at least about one minute, at least about five minutes, or at least about ten minutes and the subject's arterial blood flow was reduced but not completely occluded during the period of intraoperative hypotension; and optionally the fat emulsion is Intralipid® 20% and the dosage of Intralipid® 20% is about 10 mL to about 100 mL.

DETAILED DESCRIPTION

The present disclosure provides methods for decreasing cellular and organ injury associated with intraoperative hypotension by intravenously administering to a subject a therapeutically effective amount of a fat emulsion, following a period of intraoperative hypotension and after the subject's mean arterial blood pressure has recovered. Non-limiting examples of injuries contemplated herein include myocardial injury, myocardial infarction, and acute kidney injury. Also disclosed herein are methods for preventing injuries associated with intraoperative hypotension prior to the start of surgery, particularly for subjects that have an increased risk for intraoperative hypotension.

(a) Intraoperative Hypotension

As used herein, the term "perioperative" describes the time period describing the duration of a subject's surgical procedure commencing after admission. The perioperative period consists of a preoperative period, an intraoperative period, and a postoperative period. As used herein, the term "intraoperative" refers to a period during a surgical procedure that begins when a subject is transferred to an operating room table and ends with the transfer of the subject to a post-anesthesia care unit or intensive care unit. A "postoperative period" begins with the transfer of a subject from an operating room table to a recovery unit. As such, the postoperative period immediately follows the intraoperative period. In some embodiments, general anesthesia is used during the intraoperative period. In other embodiments, regional anesthesia is used during the intraoperative period. For example, a peripheral nerve block, a spinal block, or an epidural may be used during the intraoperative period. A sedative may optionally be used with regional anesthesia. During minimal sedation, a subject feels relaxed, can understand and answer questions, and is able to follow instructions. During moderate sedation, a subject feels drowsy and may sleep through much of the procedure, but typically is easily awakened when spoken to. During deep sedation, a subject sleeps through the procedure with little or no memory of the procedure room, breathing may slow, and the subject might sleep until the medication(s) wear off.

The term "intraoperative hypotension," as used herein, refers to a mean arterial pressure (MAP) measurement that is below 66 mmHg during an intraoperative period. Injury associated with intraoperative hypotension typically becomes more common as MAP decreases and/or with prolonged hypotension. Intraoperative hypotension may occur for at least about 30 seconds, at least about 1 minute, at least about 5 minutes, at least about 10 minutes, at least about 13 minutes, at least about 15 minutes, or more. In some aspects, intraoperative hypotension may occur for about 30 seconds to about 60 seconds. In other aspects, intraoperative hypotension may occur for about 1 minute to about 30 minutes. In other aspects, intraoperative hypotension may occur for about 1 minute to about 10 minutes, or about 1 minute to about 5 minutes. In other aspects, intraoperative hypotension may occur for about 5 minutes to about 15 minutes, or about 5 minutes to about 10 minutes. In other aspects, intraoperative hypotension may occur for about 10 minutes to about 30 minutes, or about 10 minute to about 20 minutes. In other aspects, intraoperative hypotension may occur for less than about 1 minute, less than about 5 minutes, less than about 10 minutes, less than about 13 minutes, less than about 15 minutes, less than about 20 minutes, less than about 25 minutes, or less than about 30 minutes. A subject's MAP is said to have recovered when MAP is greater than or equal to 66 mmHg. A subject's MAP can recover as result of an intervention (e.g., reperfusion therapy, etc.) or without an intervention. Methods for measuring MAP are well-known in the art.

The term "shock" refers to a state of generalized hypoperfusion where blood flow to vital organs and tissues is decreased. In one aspect, intraoperative hypotension can occur without shock. As a non-limiting example, brief and/or mild intraoperative hypotension does not imply shock. Conversely, in another aspect, shock can occur without hypotension. For example, in a setting of intense, systemic vasoconstriction, blood vessels are constricted so that perfusion (blood flow) to organs is limited despite a normal blood pressure. In still another aspect, intraoperative hypotension can occur with shock (e.g. before, after, or concurrently). For example, intraoperative hypotension can occur during pathological conditions that cause shock state, e.g., hemorrhage, anaphylaxis, cardiogenic, etc.

A "reperfusion therapy" is a medical treatment to restore blood flow, either through or around, a blockage. Reperfusion therapy includes pharmacologic reperfusion, volume infusion, and surgery. Non-limiting classes of drugs used in reperfusion therapy include thrombolytics and fibrinolytics (e.g., streptokinase, alteplase, reteplase, tenecteplase, inotropes or vasopressors to increase blood pressure and/or perfusion of vital organs, etc.). Non-limiting examples of products used for volume infusion include blood products and crystalloid or colloid solutions. Surgeries performed may be minimally-invasive endovascular procedures (e.g., coronary angioplasty, stents, etc.) or more invasive (e.g. coronary artery bypass grafting, etc.). In some instances, a subject's MAP can recover following reperfusion therapy. The terms "reperfusion therapy" and "reperfusion intervention" may be used interchangeably.

A subject of this disclosure is a human or animal that is receiving perioperative care. Suitable subjects include a human, a livestock animal, a companion animal, a laboratory animal, and a zoological animal. In a preferred embodiment, a subject is human. Also contemplated are subjects that have an increased risk of injury following intraoperative hypotension, including, but not limited to, subjects with vasoplegia, cardiovascular disease, coronary artery disease, or diabetes; subjects taking medications (e.g., angiotensin converting enzyme inhibitors, angiotensin receptor blockers, etc.); and subjects with drugs in their bloodstream that cause hemodynamic instability (e.g. cocaine).

In some aspects, intraoperative hypotension can occur during non-cardiac surgery. In these instances, a subject's blood flow can be reduced but not completely occluded during the period of intraoperative hypotension. Non-limiting causes for the ischemia include bleeding, general anesthesia, regional anesthesia (e.g., sympathectomy caused by neuraxial anesthesia, etc.), other drugs administered during surgery (e.g. sedatives, etc.), or a combination thereof. Alternatively, a subject's blood flow can be completely occluded during the period of intraoperative hypotension. In other aspects, the intraoperative hypotension can occur during cardiac surgery. In these instances, a subject's blood flow to the heart is often completely stopped.

(b) Fat Emulsion

The term "fat emulsion," as used herein, refers to a sterile, non-pyrogenic emulsion for intravenous administration comprised of water for injection and about 5% to about 50% (w/v) fat, about 10% to about 30% (w/v) fat, or about 10% to about 20% (w/v) fat. The fat can be a refined animal fat, a refined vegetable oil (e.g., soybean, canola, corn, sunflower, peanut, safflower, cottonseed, palm, etc.), a triglyceride, two or more triglycerides, or any combination thereof. Triglycerides may be saturated, unsaturated, or a combination thereof. A suitable pH for an intravenous formulation is between about pH 4 to about pH 9, preferably about pH 6 to about pH 8.9, more preferably about pH 7 to about pH 8. An exemplary pH is about pH 8. The pH may be adjusted by adding an acid or base, as is well-known in the art. The emulsified fat particles can vary in size, and are typically below about 1.0 μm, preferably about 0.5 μm or less. In some embodiments, emulsified fat particle may have diameters between about 1 nm to about 500 nm, or between about 100 nm and about 500 nm. Methods for making fat emulsions and controlling the particle size of fat emulsions are well-known in the art. See, for example, *AAPS*

*PharmSciTech* 2010, 11(4): 1526-1540, which is hereby incorporated by reference in its entirety.

In certain embodiments, a fat is refined soybean oil. The major component fatty acids of soybean oil are linoleic acid (44-62% w/v), oleic acid (19-30% w/v), palmitic acid (7-14% w/v), α-linolenic acid (4-11% w/v) and stearic acid (1.4-5.5% w/v) (Padley F B: "Major Vegetable Fats," The Lipid Handbook Gunstone F D, Harwood J L, Padley F B, eds.), Chapman and Hall Ltd., Cambridge, UK (1986), pp. 88-89.) A skilled artisan will be able to use the known fatty acid profiles of commercially available animal fats or vegetable oils to substitute these fats for soybean oil. Alternatively, synthetic triglycerides may be used to produce a fat comprising about 44% to about 62% linoleic acid, about 19% to about 30% oleic acid, about 7% to about 14% palmitic acid, about 4% to about 11% α-linolenic acid, about 1.4% to about 5.5% stearic acid.

In certain embodiments, the fat comprises about 40% to about 65% linoleic acid, about 15% to about 35% oleic acid, about 5% to about 20% palmitic acid, about 1% to about 15% α-linolenic acid, about 1% to about 10% stearic acid. In other embodiments, the fat consists of about 40% to about 65% linoleic acid, about 15% to about 35% oleic acid, about 5% to about 20% palmitic acid, about 1% to about 15% α-linolenic acid, about 1% to about 10% stearic acid. In other embodiments, the fat comprises about 44% to about 62% linoleic acid, about 19% to about 30% oleic acid, about 7% to about 14% palmitic acid, about 4% to about 11% α-linolenic acid, about 1.4% to about 5.5% stearic acid.

In some aspects, the fat emulsion may further comprise about 0.1 to about 10% (w/v) phospholipid, about 0.5% to about 5% (w/v) phospholipid, or about 1% to about 5% (w/v) phospholipid. The phospholipid can be one or more glycerophospholipid, one or more phosphosphingolipid, or any combination thereof. The phospholipid can be synthetic or natural. Common sources of industrially produced phospholipids are soya, rapeseed, sunflower, chicken eggs, bovine milk, fish eggs, etc. A preferred source is egg yolk lecithin or purified egg yolk phospholipid.

In certain embodiments, the phospholipid may be selected from phosphatidylcholine, phosphatidylethanolamine, lysophosphatidylcholine, sphingomyelin, lysophosphatidylethanolamine, phosphatidylinositol, phosphatidic acid, or any combination thereof. In other embodiments, the phospholipid may be selected from phosphatidylcholine, phosphatidylethanolamine, or a combination thereof. In an exemplary embodiment, the phospholipid comprises about 65% to about 90% (w/v) phosphatidylcholine, about 10% to about 25% (w/v) phosphatidylethanolamine, about 1% to about 5% (w/v) lysophosphatidylcholine, about 1% to about 5% (w/v) sphingomyelin, about 1% to about 5% (w/v) lysophosphatidylethanolamine, and about 2% to about 3% (w/v) phosphatidylinositol. In another exemplary embodiment, the phospholipid consists of about 65% to about 90% (w/v) phosphatidylcholine, about 10% to about 25% (w/v) phosphatidylethanolamine, about 1% to about 5% (w/v) lysophosphatidylcholine, about 1% to about 5% (w/v) sphingomyelin, about 1% to about 5% (w/v) lysophosphatidylethanolamine, and about 2% to about 3% (w/v) phosphatidylinositol. In another exemplary embodiment, the phospholipid comprises about 65% to about 90% (w/v) phosphatidylcholine and about 10% to about 35% (w/v) phosphatidylethanolamine. In another exemplary embodiment, the phospholipid consists of about 65% to about 90% (w/v) phosphatidylcholine and about 10% to about 35% (w/v) phosphatidylethanolamine. In another exemplary embodiment, the phospholipid comprises about 75% to about 85% (w/v) phosphatidylcholine and about 15% to about 25% (w/v) phosphatidylethanolamine. In another exemplary embodiment, the phospholipid consists of about 75% to about 85% (w/v) phosphatidylcholine and about 15% to about 25% (w/v) phosphatidylethanolamine.

In further aspects, the fat emulsion may also comprise about 0.5% to about 5% of a tonicity modifier, about 1% to about 5% a tonicity modifier, or about 2% to about 4% a tonicity modifier. Non-limiting examples of suitable tonicity modifiers include glycerin, sorbitol, and xylitol.

In further aspects, a fat emulsion may also comprise one or more buffering agent, antioxidant, antimicrobial agent, or any combination thereof. Non-limiting examples of suitable antioxidants include α-tocopherol, ascorbic acid, and deferoxamine mesylate. Antimicrobial agents may include, but are not limited to, EDTA, sodium benzoate, and benzyl alcohol.

In an exemplary embodiment, a fat is emulsion is Intralipid® 10%. In another exemplary embodiment, a fat is emulsion is Intralipid® 20%. In another exemplary embodiment, a fat is emulsion is Intralipid® 30%. In another exemplary embodiment, a fat emulsion comprises a combination listed in Table A below.

|   | FAT | PHOSPHOLIPID | GLYCERIN |
|---|---|---|---|
| A | about 5% to about 50% (w/v) soybean oil | | |
| B | about 5% to about 50% (w/v) soybean oil | about 0.1% to about 10% (w/v) purified egg yolk phospholipid | |
| C | about 5% to about 50% (w/v) soybean oil | about 0.1% to about 10% purified egg yolk phospholipid | about 0.5% to about 5% (w/v) glycerin |
| D | about 5% to about 50% (w/v) soybean oil | about 65% to about 90% (w/v) phosphatidylcholine, about 10% to about 25% (w/v) phosphatidylethanolamine, about 1% to about 5% (w/v) lysophosphatidylcholine, about 1% to about 5% (w/v) sphingomyelin, about 1% to about 5% (w/v) lysophosphatidylethanolamine, and about 2% to about 3% (w/v) phosphatidylinositol | |

-continued

| | FAT | PHOSPHOLIPID | GLYCERIN |
|---|---|---|---|
| E | about 5% to about 50% (w/v) soybean oil | about 65% to about 90% (w/v) phosphatidylcholine, about 10% to about 25% (w/v) phosphatidylethanolamine, about 1% to about 5% (w/v) lysophosphatidylcholine, about 1% to about 5% (w/v) sphingomyelin, about 1% to about 5% (w/v) lysophosphatidylethanolamine, and about 2% to about 3% (w/v) phosphatidylinositol | about 0.5% to about 5% (w/v) glycerin |
| F | about 5% to about 50% (w/v) soybean oil | about 65% to about 90% (w/v) phosphatidylcholine and about 10% to about 35% (w/v) phosphatidylethanolamine | |
| G | about 5% to about 50% (w/v) soybean oil | about 65% to about 90% (w/v) phosphatidylcholine and about 10% to about 35% (w/v) phosphatidylethanolamine | about 0.5% to about 5% (w/v) glycerin |
| H | about 5% to about 50% (w/v) soybean oil | about 75% to about 85% (w/v) phosphatidylcholine and about 15% to about 25% (w/v) phosphatidylethanolamine. | |
| I | about 5% to about 50% (w/v) soybean oil | about 75% to about 85% (w/v) phosphatidylcholine and about 15% to about 25% (w/v) phosphatidylethanolamine. | about 0.5% to about 5% (w/v) glycerin |
| J | about 40% to about 65% linoleic acid, about 15% to about 35% oleic acid, about 5% to about 20% palmitic acid, about 1% to about 15% α-linolenic acid, about 1% to about 10% stearic acid | | |
| K | about 40% to about 65% linoleic acid, about 15% to about 35% oleic acid, about 5% to about 20% palmitic acid, about 1% to about 15% α-linolenic acid, about 1% to about 10% stearic acid | about 0.1% to about 10% (w/v) purified egg yolk phospholipid | |
| L | about 40% to about 65% linoleic acid, about 15% to about 35% oleic acid, about 5% to about 20% palmitic acid, about 1% to about 15% α-linolenic acid, about 1% to about 10% stearic acid | about 0.1% to about 10% purified egg yolk phospholipid | about 0.5% to about 5% (w/v) glycerin |
| M | about 40% to about 65% linoleic acid, about 15% to about 35% oleic acid, about 5% to about 20% palmitic acid, about 1% to about 15% α-linolenic acid, about 1% to about 10% stearic acid | about 65% to about 90% (w/v) phosphatidylcholine, about 10% to about 25% (w/v) phosphatidylethanolamine, about 1% to about 5% (w/v) lysophosphatidylcholine, about 1% to about 5% (w/v) sphingomyelin, about 1% to about 5% (w/v) lysophosphatidylethanolamine, and about 2% to about 3% (w/v) phosphatidylinositol | |
| N | about 40% to about 65% linoleic acid, about 15% to about 35% oleic acid, about 5% to about 20% palmitic acid, about 1% to about 15% α-linolenic acid, about 1% to about 10% stearic acid | about 65% to about 90% (w/v) phosphatidylcholine, about 10% to about 25% (w/v) phosphatidylethanolamine, about 1% to about 5% (w/v) lysophosphatidylcholine, about 1% to about 5% (w/v) sphingomyelin, about 1% to about 5% (w/v) lysophosphatidylethanolamine, and about 2% to about 3% (w/v) phosphatidylinositol | about 0.5% to about 5% (w/v) glycerin |
| O | about 40% to about 65% linoleic acid, about 15% to about 35% oleic acid, about 5% to about 20% palmitic acid, about 1% to about 15% α-linolenic acid, about 1% to about 10% stearic acid | about 65% to about 90% (w/v) phosphatidylcholine and about 10% to about 35% (w/v) phosphatidylethanolamine | |
| P | about 40% to about 65% linoleic acid, about 15% to about 35% oleic acid, about 5% to about 20% palmitic acid, about 1% to about 15% α-linolenic acid, about 1% to about 10% stearic acid | about 65% to about 90% (w/v) phosphatidylcholine and about 10% to about 35% (w/v) phosphatidylethanolamine | about 0.5% to about 5% (w/v) glycerin |

| | FAT | PHOSPHOLIPID | GLYCERIN |
|---|---|---|---|
| Q | about 40% to about 65% linoleic acid, about 15% to about 35% oleic acid, about 5% to about 20% palmitic acid, about 1% to about 15% α-linolenic acid, about 1% to about 10% stearic acid | about 75% to about 85% (w/v) phosphatidylcholine and about 15% to about 25% (w/v) phosphatidylethanolamine. | |
| R | about 40% to about 65% linoleic acid, about 15% to about 35% oleic acid, about 5% to about 20% palmitic acid, about 1% to about 15% α-linolenic acid, about 1% to about 10% stearic acid | about 75% to about 85% (w/v) phosphatidylcholine and about 15% to about 25% (w/v) phosphatidylethanolamine. | about 0.5% to about 5% (w/v) glycerin |
| S | about 44% to about 62% linoleic acid, about 19% to about 30% oleic acid, about 7% to about 14% palmitic acid, about 4% to about 11% α-linolenic acid, about 1.4% to about 5.5% stearic acid | | |
| T | about 44% to about 62% linoleic acid, about 19% to about 30% oleic acid, about 7% to about 14% palmitic acid, about 4% to about 11% α-linolenic acid, about 1.4% to about 5.5% stearic acid | about 0.1% to about 10% (w/v) purified egg yolk phospholipid | |
| U | about 44% to about 62% linoleic acid, about 19% to about 30% oleic acid, about 7% to about 14% palmitic acid, about 4% to about 11% α-linolenic acid, about 1.4% to about 5.5% stearic acid | about 0.1% to about 10% purified egg yolk phospholipid | about 0.5% to about 5% (w/v) glycerin |
| V | about 44% to about 62% linoleic acid, about 19% to about 30% oleic acid, about 7% to about 14% palmitic acid, about 4% to about 11% α-linolenic acid, about 1.4% to about 5.5% stearic acid | about 65% to about 90% (w/v) phosphatidylcholine, about 10% to about 25% (w/v) phosphatidylethanolamine, about 1% to about 5% (w/v) lysophosphatidylcholine, about 1% to about 5% (w/v) sphingomyelin, about 1% to about 5% (w/v) lysophosphatidylethanolamine, and about 2% to about 3% (w/v) phosphatidylinositol | |
| W | about 44% to about 62% linoleic acid, about 19% to about 30% oleic acid, about 7% to about 14% palmitic acid, about 4% to about 11% α-linolenic acid, about 1.4% to about 5.5% stearic acid | about 65% to about 90% (w/v) phosphatidylcholine, about 10% to about 25% (w/v) phosphatidylethanolamine, about 1% to about 5% (w/v) lysophosphatidylcholine, about 1% to about 5% (w/v) sphingomyelin, about 1% to about 5% (w/v) lysophosphatidylethanolamine, and about 2% to about 3% (w/v) phosphatidylinositol | about 0.5% to about 5% (w/v) glycerin |
| X | about 44% to about 62% linoleic acid, about 19% to about 30% oleic acid, about 7% to about 14% palmitic acid, about 4% to about 11% α-linolenic acid, about 1.4% to about 5.5% stearic acid | about 65% to about 80% (w/v) phosphatidylcholine and about 10% to about 35% (w/v) phosphatidylethanolamine | |
| Y | about 44% to about 62% linoleic acid, about 19% to about 30% oleic acid, about 7% to about 14% palmitic acid, about 4% to about 11% α-linolenic acid, about 1.4% to about 5.5% stearic acid | about 65% to about 80% (w/v) phosphatidylcholine and about 10% to about 35% (w/v) phosphatidylethanolamine | about 0.5% to about 5% (w/v) glycerin |
| Z | about 44% to about 62% linoleic acid, about 19% to about 30% oleic acid, about 7% to about 14% palmitic acid, about 4% to about 11% α-linolenic acid, about 1.4% to about 5.5% stearic acid | about 75% to about 85% (w/v) phosphatidylcholine and about 15% to about 25% (w/v) phosphatidylethanolamine. | |
| AA | about 44% to about 62% linoleic acid, about 19% to about 30% oleic acid, about 7% to about 14% palmitic acid, about 4% to about 11% α-linolenic acid, about 1.4% to about 5.5% stearic acid | about 75% to about 85% (w/v) phosphatidylcholine and about 15% to about 25% (w/v) phosphatidylethanolamine. | about 0.5% to about 5% (w/v) glycerin |

(c) Administration

A therapeutically effective amount of a fat emulsion is intravenously administered to a subject. As used herein, the term "therapeutically effective amount" means an amount of a substance (e.g., a fat emulsion) that leads to measurable and beneficial effects for the subject administered the substance, i.e., significant efficacy. In one aspect, administration can occur before surgery begins, with the first incision marking the start of surgery. For example, administration may occur about one minute before surgery, about five minutes before surgery, about ten minutes before surgery, about thirty minutes before surgery or more. In another example, administration may occur about one hour, about two hours, or about four hours before surgery. In still another example, administration may occur about six hours, about twelve hours, about eighteen hours or about twenty-four hours before administration. Administration before surgery may be desirable for all subjects, or only for subjects at greater risk for intraoperative hypotension. In another aspect, administration can occur intraoperatively, following intraoperative hypotension and after the subject's MAP is greater than or equal to 66 mmHg, preferably for at least about one minute. In another aspect, administration can occur postoperatively following intraoperative hypotension, provided the subject's MAP is greater than or equal to 66 mmHg. In another aspect, administration can occur as any combination of before surgery; intraoperatively following intraoperative hypotension and after the subject's MAP is greater than or equal to 66 mmHg; and postoperatively following intraoperative hypotension, provided the subject's MAP is greater than or equal to 66 mmHg.

A therapeutically effective amount of a fat emulsion, i.e. a dose, may be administered to the subject as a bolus, as an infusion, or as a combination of a bolus or loading dose followed by an infusion. When administered as a bolus, a dose may be administered all at once, or the dose may be divided into smaller doses (e.g., 1, 2, 3, or more) and administered at regular intervals (e.g., minutes or hours) or over a given timeframe (e.g., the remainder of the intraoperative period). When administered as an infusion, the infusion can occur at a single rate or the rate can vary. A single dose or multiple doses may be administered.

A therapeutically effective amount, or dose, of a fat emulsion administered according to this disclosure can be determined using standard clinical techniques and may be influenced by the circumstances surrounding the case, including the amount of the fat in the emulsion and its composition, the amount of the decrease in the subject's MAP and/or the duration of the intraoperative hypotension, or the stability of the subject's MAP at the time of administration, among other considerations. For example, in embodiments where the fat emulsion is Intralipid® 20%, a suitable dose will typically be less than about 250 mL. In some examples, a suitable dose may be about 1 mL to about 250 mL, about 10 mL to about 250 mL, about 50 mL to about 250 mL, or about 100 mL to about 250 mL. In some examples, a suitable dose may be about 10 mL to about 100 mL. In other examples, a suitable dose may be about 10 mL to about 50 mL or about 50 mL to about 100 mL. In other examples, a suitable dose may be about 100 mL to about 150 mL or about 150 mL to about 200 mL. In other examples, a suitable dose may be about 10 mL to about 35 mL, about 25 mL to about 50 mL, about 35 mL to about 60 mL, about 50 mL to about 75 mL, about 60 mL to about 85 mL, about 75 mL to about 100 mL, about 85 mL to about 110 mL, about 100 mL to about 125 mL, about 110 mL to about 135 mL, or about 125 mL to about 150 mL. In other examples, a suitable dose may be about 10 mL, about 15 mL, about 20 mL, about 25 mL, about 30 mL, about 35 mL, about 40 mL, about 45 mL, about 50 mL, about 55 mL, about 60 mL, about 65 mL, about 70 mL, about 75 mL, about 80 mL, about 85 mL, about 90 mL, about 95 mL, about 100 mL, about 105 mL, about 110 mL, about 115 mL, about 120 mL, or about 125 mL. Based on these disclosures for Intralipid® 20%, a skilled artisan will be able to determine suitable doses for other fat emulsions described in Section (b).

(d) Control Group

Injury and/or mortality are decreased in a subject as compared to a control group. A control group, as used herein, refers to a plurality of subjects that were not administered a fat emulsion and that would have included the subject. Criteria for identifying a suitable control group may include age, gender, comorbidities, types of surgery, etc.

(e) Myocardial Injury and Acute Kidney Injury

Myocardial injury and acute kidney injury are two examples of injuries associated with intraoperative hypotension, and the present disclosure provides methods for preventing and/or decreasing myocardial injury and/or acute kidney injury in a subject. As used herein, the term "preventing" refers to both complete prevention (i.e. no injury occurs) or a decrease in injury as compared to a control group that did not receive the fat emulsion before surgery (i.e. prevention of some amount of injury).

In one aspect, the present disclosure provides methods for preventing myocardial injury and/or acute kidney injury in a subject. The method comprises intravenously administering to a subject, before surgery begins, a therapeutically effective amount of a fat emulsion. Suitable fat emulsions are detailed above in Section (b), and details of their administration are described in Section (c). In an exemplary embodiment, a fat emulsion comprises a combination listed in Table A. In another exemplary embodiment, a fat emulsion consists of a combination listed in Table A. In another exemplary embodiment, a fat emulsion is Intralipid® 10%, Intralipid® 20%, or Intralipid® 30%. Suitable subjects have a mean arterial pressure (MAP) greater than or equal to 66 mmHg at the time of administration, and are further described above in Section (a). In certain embodiments, the subject has a greater risk for intraoperative hypotension. Non-limiting examples of subjects at greater risk for intraoperative hypotension include subjects under general or regional anesthesia that also have: a prior history of intraoperative hypotension, have vasoplegia, have cardiovascular disease, have coronary artery disease, have diabetes, are taking angiotensin converting enzyme inhibitors, are taking angiotensin receptor blockers, and/or have drugs in their bloodstream that cause hemodynamic instability including but not limited to cocaine.

In another aspect, the present disclosure provides methods for decreasing myocardial injury and/or acute kidney injury in a subject following intraoperative hypotension, wherein the intraoperative hypotension occurred with or without shock. Suitable subjects are described above in Section (a), and includes subjects that were administered a dose of the fat emulsion before surgery. In some aspects, the intraoperative hypotension occurred during non-cardiac surgery and the subject's blood flow was reduced but not completely occluded during the period of intraoperative hypotension. In other aspects, the intraoperative hypotension occurred during non-cardiac surgery and the subject's blood flow was completely occluded during the period of intraoperative hypotension. In still other aspects, the intraoperative hypotension occurred during cardiac surgery. In aspects involving non-cardiac surgery, the subject may be under general anesthesia or regional anesthesia during the surgical procedure. In aspects involving cardiac surgery, the subject is under general anesthesia during the surgical procedure. The method comprises intravenously administering to the subject a therapeutically effective amount of a fat emulsion after the subject's mean arterial pressure (MAP) is recovered to greater than or equal to 66 mmHg. The fat emulsion can be administered intraoperatively or postoperatively, preferably during the intraoperative period but after the subject's MAP recovered. Suitable fat emulsions are detailed above in Section (b), and details of their administration are described in Section (c). In an exemplary embodiment, a fat emulsion comprises a combination listed in Table A. In another exemplary embodiment, a fat emulsion consists of a combination listed in Table A. In another exemplary embodiment, a fat emulsion is Intralipid® 10%, Intralipid® 20%, or Intralipid® 30%.

In another aspect, the present disclosure provides methods for preventing myocardial injury and/or acute kidney injury in a subject following general and/or regional anesthesia. The method comprises intravenously administering to a subject, before surgery begins, a therapeutically effective amount of a fat emulsion. Suitable fat emulsions are detailed above in Section (b), and details of their administration are described in Section (c). In an exemplary embodiment, a fat emulsion comprises a combination listed in Table A. In another exemplary embodiment, a fat emulsion consists of a combination listed in Table A. In another exemplary embodiment, a fat emulsion is Intralipid® 10%, Intralipid® 20%, or Intralipid® 30%. Suitable subjects have a mean arterial pressure (MAP) greater than or equal to 66 mmHg, and are further described above in Section (a). In certain embodiments, the subject has a greater risk for intraoperative hypotension. Non-limiting examples of subjects at greater risk for intraoperative hypotension include subjects with a prior history of intraoperative hypotension, subjects with vasoplegia, subjects with cardiovascular disease, subjects coronary artery disease, subjects diabetes, subjects angiotensin converting enzyme inhibitors, subjects taking angiotensin receptor blockers, subjects with drugs in their bloodstream that cause hemodynamic instability including but not limited to cocaine.

In another aspect, the present disclosure provides methods for decreasing myocardial injury and/or acute kidney injury following general and/or regional anesthesia. The method comprises intravenously administering to a subject that is not in shock, and/or was not in shock, a therapeutically effective amount of a fat emulsion after the subject has received one or more reperfusion therapies to restore the subject's mean arterial pressure (MAP) to 66 mmHg or greater. Suitable subjects are described above in Section (a). Suitable fat emulsions are detailed above in Section (b), and details of their administration are described in Section (c). In an exemplary embodiment, a fat emulsion comprises a combination listed in Table A. In another exemplary embodiment, a fat emulsion consists of a combination listed in Table A. In another exemplary embodiment, a fat emulsion is Intralipid® 10%, Intralipid® 20%, or Intralipid® 30%. The fat emulsion can be administered intraoperatively or postoperatively, preferably during the intraoperative period but after the subject's MAP recovered.

In each of the above aspects, the marker(s) to be measured will vary depending upon the type of injury. Preferred markers are accessible, sensitive, and specific to the type of injury. Specificity may be increased by using more than one marker. Accessible markers of myocardial injury are typically in blood or serum, while accessible markers of acute kidney injury are typically in blood, serum or urine. Marker(s) of myocardial injury may be measured alone or in combination with marker(s) of other types of injury (including but not limited to acute kidney injury) and/or marker(s) of inflammation.

Suitable markers of myocardial injury are known in the art, as are methods for determining their concentration in biological fluids. In some embodiments, the marker of myocardial injury is cardiac troponin, heart-type fatty acid binding protein, or a combination thereof. "Cardiac troponin" refers to tissue-specific isoforms of the troponin I or troponin T that are found in cardiac muscle. The cardiac-specific isoforms of troponin I and troponin T are abbreviated cTnI and cTnT, respectively. Heart-type fatty acid binding protein (hFABP) may also be known as mammary-derived growth inhibitor. In humans, cTnI is encoded by TNNI3, cTnT is encoded by TNNT2, and hFABP is encoded by FABP3. Homologs in other animals may be readily identified by methods known in the art. Non-limiting examples of other markers of myocardial injury include myoglobin, aspartate amino-transferase, creatine kinase, CK-MB, lactate dehydrogenase, ischemic-modified albumin, pro-brain natriuretic peptide, glycogen phosphorylase BB, ST2, C-terminal pro-endothelin 1, mid regional pro-adrenomedullin, copeptin, and the ratio of myoglobin to carbonic anhydrase III. Immunoassays and other epitope-based detection methods are routinely used in the pharmaceutical arts to detect and quantify markers of myocardial injury. For example, commercial immunoassays are available to measure serum concentrations cardiac troponin and hFABP. Enzyme measurements mays also be used (e.g., enzyme-substrate-based colorimetric assays followed by measurement using a spectrophotometer, etc.). Markers of myocardial injury are typically detected in blood or serum, though other biological fluids may be used.

Suitable markers of acute kidney injury are also known in the art, as are methods for determining their concentration in biological fluids. See, for example, *Annu Rev Pharmacol Toxicol,* 2008; 48: 463-493. Markers of acute kidney injury are typically detected in blood, serum, or urine. In some embodiments, the marker of acute kidney injury is creatinine or lipocalin-2. Elevated creatinine levels signify impaired kidney function. A more precise measure of the kidney function can be estimated by calculating how much creatinine is cleared from the body by the kidneys. This is referred to as creatinine clearance and it estimates the rate of filtration by kidneys (glomerular filtration rate, or GFR). The creatinine clearance can be measured in two ways. It can be calculated by a formula using serum (blood) creatinine level, patient's weight, and age. Creatinine clearance can also be more directly measured by collecting a 24-hour urine sample and then drawing a blood sample. The creatinine levels in both urine and blood are determined and compared. Lipocalin-2, also known as neutrophil gelatinase-associated lipocalin, is used as a marker of kidney injury. Lipocalin-2 is encoded by LCN2. Lipocalin-2 is secreted into the blood and urine within about 2 hours of injury. Blood urea nitrogen (BUN) level is another indicator of kidney function. Urea is also a metabolic byproduct which can build up if kidney function is impaired. The BUN-to-creatinine ratio generally provides more precise information about kidney function and its possible underlying cause compared with creatinine level alone. Non-limiting examples of other markers of acute kidney injury include N-acetyl-β-glucosaminidase, β2-microglobulin or fragments thereof, α1-microglobulin, retinol binding protein, cystatin-c, microalbumin, kidney injury molecule-1, clusterin, interleukine-18, cysteine-rich protein, osteopontin, liver-type fatty acid-binding protein, sodium/hydrogen exchanger isoform (NHE3), and fetuin A. Immunoassays and other epitope-based detection methods are routinely used in the pharmaceutical arts to detect and quantify markers of acute kidney injury. Enzyme measurements mays also be used (e.g., enzyme-substrate-based colorimetric assays followed by measurement using a spectrophotometer, etc.).

The timing for detecting a change in the biomarker may depend on how quickly the marker is found in the biological fluid after injury and the type of test. For example, serum creatinine measurements can be taken more frequently than a 24-hour urine test, which requires 24-hours of urine collection. Timing may also be affected by the sensitivity of an assay. For example, current assays can detect cardiac troponins in blood about 2-4 hours after onset of damage, whereas cardiac troponin was not detected by older generation assays until about 6-12 hours after onset of myocardial injury. Timing may be expressed relative to when the fat emulsion was first administered ("about X amount of time after administration"), relative to the start of postoperative period ("about X amount of time postoperatively"), or relative to the start of some other clinical milestone (e.g. discharge, etc.). A skilled artisan using a milestone not expressly stated will be able to adjust the timing according to the disclosures herein.

In some embodiments, about two to about six hours after administration (e.g., about 2, about 3, about 4, about 5, about 6 hours), the therapeutically effective amount of the fat emulsion decreases a marker of myocardial injury selected from serum cardiac troponin, serum heart-type fatty acid binding protein, or a combination thereof, by at least 10% at as compared to a control group that did not receive the fat emulsion. For example, the marker may be decreased by about 10%, about 20%, about 30%, about 40%, or about 50%. In another example, the marker may be decreased by about 60%, about 70%, about 80%, about 90%, or about 100%. In still another example, 24-hour postoperative mortality may be decreased by about 2-fold, about 3-fold, about 4-fold, about 5-fold, about 10-fold, or more.

In some embodiments, about six hours to about twelve hours after administration (e.g., about 6, about 7, about 8, about 9, about 10 hours), the therapeutically effective amount of the fat emulsion decreases a marker of myocardial injury selected from serum cardiac troponin, serum heart-type fatty acid binding protein, or a combination thereof, by at least 10% at as compared to a control group that did not receive the fat emulsion. For example, the marker may be decreased by about 10%, about 20%, about 30%, about 40%, or about 50%. In another example, the marker may be decreased by about 60%, about 70%, about 80%, about 90%, or about 100%. In still another example, 24-hour postoperative mortality may be decreased by about 2-fold, about 3-fold, about 4-fold, about 5-fold, about 10-fold, or more.

In some embodiments, about twelve hours to about twenty-four hours after administration (e.g., about 12, about 13, about 14, about 15, about 16, about 17, about 18, about 19, about 20, about 21, about 22, about 23, about 24 hours), the therapeutically effective amount of the fat emulsion decreases a marker of myocardial injury selected from serum cardiac troponin, serum heart-type fatty acid binding protein, or a combination thereof, by at least 10% at as compared to a control group that did not receive the fat emulsion. For example, the marker may be decreased by about 10%, about 20%, about 30%, about 40%, or about 50%. In another example, the marker may be decreased by about 60%, about 70%, about 80%, about 90%, or about 100%. In still another example, 24-hour postoperative mortality may be decreased by about 2-fold, about 3-fold, about 4-fold, about 5-fold, about 10-fold, or more.

In some embodiments, about one week to two weeks after administration (e.g., about 7, about 8, about 9, about 10, about 11, about 12, about 13, about 14 days), the therapeutically effective amount of the fat emulsion decreases a marker of myocardial injury selected from serum cardiac troponin, serum heart-type fatty acid binding protein, or a combination thereof, by at least 10% at as compared to a control group that did not receive the fat emulsion. For example, the marker may be decreased by about 10%, about 20%, about 30%, about 40%, or about 50%. In another example, the marker may be decreased by about 60%, about 70%, about 80%, about 90%, or about 100%. In still another example, 24-hour postoperative mortality may be decreased by about 2-fold, about 3-fold, about 4-fold, about 5-fold, about 10-fold, or more.

In some embodiments, about one month after administration, the therapeutically effective amount of the fat emulsion decreases a marker of myocardial injury selected from serum cardiac troponin, serum heart-type fatty acid binding protein, or a combination thereof, by at least 10% at as compared to a control group that did not receive the fat emulsion. For example, the marker may be decreased by about 10%, about 20%, about 30%, about 40%, or about 50%. In another example, the marker may be decreased by about 60%, about 70%, about 80%, about 90%, or about 100%. In still another example, 24-hour postoperative mortality may be decreased by about 2-fold, about 3-fold, about 4-fold, about 5-fold, about 10-fold, or more.

In some embodiments, about two to about six hours postoperatively (e.g., about 2, about 3, about 4, about 5, about 6 hours), the therapeutically effective amount of the fat emulsion decreases a marker of myocardial injury selected from serum cardiac troponin, serum heart-type fatty acid binding protein, or a combination thereof, by at least 10% at as compared to a control group that did not receive the fat emulsion. For example, the marker may be decreased by about 10%, about 20%, about 30%, about 40%, or about 50%. In another example, the marker may be decreased by about 60%, about 70%, about 80%, about 90%, or about 100%. In still another example, 24-hour postoperative mortality may be decreased by about 2-fold, about 3-fold, about 4-fold, about 5-fold, about 10-fold, or more.

In some embodiments, about six hours to about twelve hours postoperatively (e.g., about 6, about 7, about 8, about 9, about 10 hours), the therapeutically effective amount of the fat emulsion decreases a marker of myocardial injury selected from serum cardiac troponin, serum heart-type fatty acid binding protein, or a combination thereof, by at least 10% at as compared to a control group that did not receive the fat emulsion. For example, the marker may be decreased by about 10%, about 20%, about 30%, about 40%, or about 50%. In another example, the marker may be decreased by about 60%, about 70%, about 80%, about 90%, or about 100%. In still another example, 24-hour postoperative mortality may be decreased by about 2-fold, about 3-fold, about 4-fold, about 5-fold, about 10-fold, or more.

In some embodiments, about twelve hours to about twenty-four hours postoperatively (e.g., about 12, about 13, about 14, about 15, about 16, about 17, about 18, about 19, about 20, about 21, about 22, about 23, about 24 hours), the therapeutically effective amount of the fat emulsion decreases a marker of myocardial injury selected from serum cardiac troponin, serum heart-type fatty acid binding protein, or a combination thereof, by at least 10% at as compared to a control group that did not receive the fat emulsion. For example, the marker may be decreased by about 10%, about 20%, about 30%, about 40%, or about 50%. In another example, the marker may be decreased by about 60%, about 70%, about 80%, about 90%, or about 100%. In still another example, 24-hour postoperative mortality may be decreased by about 2-fold, about 3-fold, about 4-fold, about 5-fold, about 10-fold, or more.

In some embodiments, about one week to two weeks postoperatively (e.g., about 7, about 8, about 9, about 10, about 11, about 12, about 13, about 14 days), the therapeutically effective amount of the fat emulsion decreases a marker of myocardial injury selected from serum cardiac troponin, serum heart-type fatty acid binding protein, or a combination thereof, by at least 10% at as compared to a control group that did not receive the fat emulsion. For example, the marker may be decreased by about 10%, about 20%, about 30%, about 40%, or about 50%. In another example, the marker may be decreased by about 60%, about 70%, about 80%, about 90%, or about 100%. In still another example, 24-hour postoperative mortality may be decreased by about 2-fold, about 3-fold, about 4-fold, about 5-fold, about 10-fold, or more.

In some embodiments, about one month postoperatively, the therapeutically effective amount of the fat emulsion decreases a marker of myocardial injury selected from serum cardiac troponin, serum heart-type fatty acid binding protein, or a combination thereof, by at least 10% at as compared to a control group that did not receive the fat emulsion. For example, the marker may be decreased by about 10%, about 20%, about 30%, about 40%, or about 50%. In another example, the marker may be decreased by about 60%, about 70%, about 80%, about 90%, or about 100%. In still another example, 24-hour postoperative mortality may be decreased by about 2-fold, about 3-fold, about 4-fold, about 5-fold, about 10-fold, or more.

In each of the above embodiments, the decrease may also be expressed as a fold-change, for example, about 2-fold, about 3-fold, about 4-fold, about 5-fold, about 10-fold, or more. The percent decrease or fold-change may also be expressed as a range. For example, the decrease may be between about 10% and about 50%, between about 25% and about 75%, between about 50% and about 100%, between about 75% and about 125%, between about 1-100 fold, about 1-10 fold, about 1-5 fold, about 1-4 fold, about 1-3 fold, or about 1-2 fold. Alternatively, the decrease may be between about 10% and about 30%, between about 20% and about 40%, between about 30% and about 50%, between about 40% and about 60%, between about 50% and about 70%, between about 60% and about 80%, between about 70% and about 90%, or between about 80% and about 100%.

(f) Myocardial Infarction

The present disclosure also provides methods for preventing and/or decreasing postoperative myocardial infarction. The term "decreasing postoperative myocardial infarction" refers to decreasing a relative risk of myocardial infarction and/or decreasing a number of myocardial infarctions.

In one aspect, the present disclosure provides methods for preventing postoperative myocardial infarction in a subject. The method comprises intravenously administering to a subject, before surgery begins, a therapeutically effective amount of a fat emulsion. Suitable fat emulsions are detailed above in Section (b), and details of their administration are described in Section (c). In an exemplary embodiment, a fat emulsion comprises a combination listed in Table A. In another exemplary embodiment, a fat emulsion consists of a combination listed in Table A. In another exemplary embodiment, a fat emulsion is Intralipid® 10%, Intralipid® 20%, or Intralipid® 30%. Suitable subjects have a mean arterial pressure (MAP) greater than or equal to 66 mmHg at the time of administration, and are further described above in Section (a). In certain embodiments, the subject has a greater risk for intraoperative hypotension. Non-limiting examples of subjects at greater risk for intraoperative hypotension include subjects under general or regional anesthesia that also have: a prior history of intraoperative hypotension, have vasoplegia, have cardiovascular disease, have coronary artery disease, have diabetes, are taking angiotensin converting enzyme inhibitors, are taking angiotensin receptor blockers, and/or have drugs in their bloodstream that cause hemodynamic instability including but not limited to cocaine.

In another aspect, the present disclosure provides methods for decreasing postoperative myocardial infarction in a subject following intraoperative hypotension. Suitable subjects are described above in in Section (a). In further aspects, the intraoperative hypotension occurred during non-cardiac surgery and the subject's blood flow was reduced but not completely occluded during the period of intraoperative hypotension. In other aspects, the intraoperative hypotension occurred during non-cardiac surgery and the subject's blood flow was completely occluded during the period of intraoperative hypotension. In still other aspects, the intraoperative hypotension occurred during cardiac surgery. In aspects involving non-cardiac surgery, the subject may be under general anesthesia or regional anesthesia during the surgical procedure. In aspects involving cardiac surgery, the subject is under general anesthesia during the surgical procedure. The method comprises intravenously administering to the subject a therapeutically effective amount of a fat emulsion after the subject's mean arterial pressure (MAP) is recovered to greater than or equal to 66 mmHg. The fat emulsion can be administered intraoperatively or postoperatively, preferably during the intraoperative period but after the subject's MAP recovered. Suitable fat emulsions are detailed above in in Section (b), and details of their administration are described in Section (c). In an exemplary embodiment, a fat emulsion comprises a combination listed in Table A. In another exemplary embodiment, a fat emulsion consists of a combination listed in Table A. In another exemplary embodiment, a fat emulsion is Intralipid® 10%, Intralipid® 20%, or Intralipid® 30%.

In another aspect, the present disclosure provides methods for preventing postoperative myocardial infarction following general anesthesia. The method comprises intravenously administering to a subject, before surgery begins, a therapeutically effective amount of a fat emulsion. Suitable fat emulsions are detailed above in Section (b), and details of their administration are described in Section (c). In an exemplary embodiment, a fat emulsion comprises a combination listed in Table A. In another exemplary embodiment, a fat emulsion consists of a combination listed in Table A. In another exemplary embodiment, a fat emulsion is Intralipid® 10%, Intralipid® 20%, or Intralipid® 30%. Suitable subjects have a mean arterial pressure (MAP) greater than or equal to 66 mmHg, and are further described above in Section (a). In certain embodiments, the subject has a greater risk for intraoperative hypotension. Non-limiting examples of subjects at greater risk for intraoperative hypotension include subjects with a prior history of intraoperative hypotension, subjects with vasoplegia, subjects with cardiovascular disease, subjects coronary artery disease, subjects diabetes, subjects angiotensin converting enzyme inhibitors, subjects taking angiotensin receptor blockers, subjects with drugs in their bloodstream that cause hemodynamic instability including but not limited to cocaine.

In another aspect, the present disclosure provides methods for decreasing postoperative myocardial infarction following general anesthesia. The method comprises intravenously administering to a subject that is not in shock, and/or was not in shock, a therapeutically effective amount of a fat emulsion after the subject has received one or more reperfusion therapies to restore the subject's mean arterial pressure (MAP) to 66 mmHg or greater. The fat emulsion can be administered intraoperatively or postoperatively, preferably during the intraoperative period but after the subject's MAP recovered. Suitable subjects are described above in Section (a). Suitable fat emulsions are detailed above in Section (b), and details of their administration are described in Section (c). In an exemplary embodiment, a fat emulsion comprises a combination listed in Table A. In another exemplary embodiment, a fat emulsion consists of a combination listed in Table A. In another exemplary embodiment, a fat emulsion is Intralipid® 10%, Intralipid® 20%, or Intralipid® 30%.

In each of the above aspects, a decrease in postoperative myocardial infarction may be seen at one or more times prior to discharge (e.g., about 2 hours postoperatively to discharge), at one or more times following discharge (e.g., discharge to about 12 months postoperatively), or a combination thereof. Timing may be expressed relative to when the fat emulsion was first administered ("about X amount of time after administration"), relative to the start of postoperative period ("about X amount of time postoperatively"), or relative to the start of some other clinical milestone (e.g. discharge, etc.). A skilled artisan using a milestone not expressly stated will be able to adjust the timing according to the disclosures herein.

In some embodiments, about two to about six hours after administration (e.g., about 2, about 3, about 4, about 5, about 6 hours), the therapeutically effective amount of the fat emulsion decreases a marker of myocardial injury selected from serum cardiac troponin, serum heart-type fatty acid binding protein, or a combination thereof, by at least 10% at as compared to a control group that did not receive the fat emulsion. For example, the marker may be decreased by about 10%, about 20%, about 30%, about 40%, or about 50%. In another example, the marker may be decreased by about 60%, about 70%, about 80%, about 90%, or about 100%. In still another example, 24-hour postoperative mortality may be decreased by about 2-fold, about 3-fold, about 4-fold, about 5-fold, about 10-fold, or more.

In some embodiments, about six hours to about twelve hours after administration (e.g., about 6, about 7, about 8, about 9, about 10 hours), the therapeutically effective amount of the fat emulsion decreases a marker of myocardial injury selected from serum cardiac troponin, serum heart-type fatty acid binding protein, or a combination thereof, by at least 10% at as compared to a control group that did not receive the fat emulsion. For example, the marker may be decreased by about 10%, about 20%, about 30%, about 40%, or about 50%. In another example, the marker may be decreased by about 60%, about 70%, about 80%, about 90%, or about 100%. In still another example, 24-hour postoperative mortality may be decreased by about 2-fold, about 3-fold, about 4-fold, about 5-fold, about 10-fold, or more.

In some embodiments, about twelve hours to about twenty-four hours after administration (e.g., about 12, about 13, about 14, about 15, about 16, about 17, about 18, about 19, about 20, about 21, about 22, about 23, about 24 hours), the therapeutically effective amount of the fat emulsion decreases a marker of myocardial injury selected from serum cardiac troponin, serum heart-type fatty acid binding protein, or a combination thereof, by at least 10% at as compared to a control group that did not receive the fat emulsion. For example, the marker may be decreased by about 10%, about 20%, about 30%, about 40%, or about 50%. In another example, the marker may be decreased by about 60%, about 70%, about 80%, about 90%, or about 100%. In still another example, 24-hour postoperative mortality may be decreased by about 2-fold, about 3-fold, about 4-fold, about 5-fold, about 10-fold, or more.

In some embodiments, about one week to two weeks after administration (e.g., about 7, about 8, about 9, about 10, about 11, about 12, about 13, about 14 days), the therapeutically effective amount of the fat emulsion decreases a marker of myocardial injury selected from serum cardiac troponin, serum heart-type fatty acid binding protein, or a combination thereof, by at least 10% at as compared to a control group that did not receive the fat emulsion. For example, the marker may be decreased by about 10%, about 20%, about 30%, about 40%, or about 50%. In another example, the marker may be decreased by about 60%, about 70%, about 80%, about 90%, or about 100%. In still another example, 24-hour postoperative mortality may be decreased by about 2-fold, about 3-fold, about 4-fold, about 5-fold, about 10-fold, or more.

In some embodiments, about one month after administration, the therapeutically effective amount of the fat emulsion decreases a marker of myocardial injury selected from serum cardiac troponin, serum heart-type fatty acid binding protein, or a combination thereof, by at least 10% at as compared to a control group that did not receive the fat emulsion. For example, the marker may be decreased by about 10%, about 20%, about 30%, about 40%, or about 50%. In another example, the marker may be decreased by about 60%, about 70%, about 80%, about 90%, or about 100%. In still another example, 24-hour postoperative mortality may be decreased by about 2-fold, about 3-fold, about 4-fold, about 5-fold, about 10-fold, or more.

In some embodiments, about two to about six hours postoperatively (e.g., about 2, about 3, about 4, about 5, about 6 hours), the therapeutically effective amount of the fat emulsion decreases a marker of myocardial injury selected from serum cardiac troponin, serum heart-type fatty acid binding protein, or a combination thereof, by at least 10% at as compared to a control group that did not receive the fat emulsion. For example, the marker may be decreased by about 10%, about 20%, about 30%, about 40%, or about 50%. In another example, the marker may be decreased by about 60%, about 70%, about 80%, about 90%, or about 100%. In still another example, 24-hour postoperative mortality may be decreased by about 2-fold, about 3-fold, about 4-fold, about 5-fold, about 10-fold, or more.

In some embodiments, about six hours to about twelve hours postoperatively (e.g., about 6, about 7, about 8, about 9, about 10 hours), the therapeutically effective amount of the fat emulsion decreases a marker of myocardial injury selected from serum cardiac troponin, serum heart-type fatty acid binding protein, or a combination thereof, by at least 10% at as compared to a control group that did not receive the fat emulsion. For example, the marker may be decreased by about 10%, about 20%, about 30%, about 40%, or about 50%. In another example, the marker may be decreased by about 60%, about 70%, about 80%, about 90%, or about 100%. In still another example, 24-hour postoperative mortality may be decreased by about 2-fold, about 3-fold, about 4-fold, about 5-fold, about 10-fold, or more.

In some embodiments, about twelve hours to about twenty-four hours postoperatively (e.g., about 12, about 13, about 14, about 15, about 16, about 17, about 18, about 19, about 20, about 21, about 22, about 23, about 24 hours), the therapeutically effective amount of the fat emulsion decreases a marker of myocardial injury selected from serum cardiac troponin, serum heart-type fatty acid binding protein, or a combination thereof, by at least 10% at as compared to a control group that did not receive the fat emulsion. For example, the marker may be decreased by about 10%, about 20%, about 30%, about 40%, or about 50%. In another example, the marker may be decreased by about 60%, about 70%, about 80%, about 90%, or about 100%. In still another example, 24-hour postoperative mortality may be decreased by about 2-fold, about 3-fold, about 4-fold, about 5-fold, about 10-fold, or more.

In some embodiments, about one week to two weeks postoperatively (e.g., about 7, about 8, about 9, about 10, about 11, about 12, about 13, about 14 days), the therapeutically effective amount of the fat emulsion decreases a marker of myocardial injury selected from serum cardiac troponin, serum heart-type fatty acid binding protein, or a combination thereof, by at least 10% at as compared to a control group that did not receive the fat emulsion. For example, the marker may be decreased by about 10%, about 20%, about 30%, about 40%, or about 50%. In another example, the marker may be decreased by about 60%, about 70%, about 80%, about 90%, or about 100%. In still another example, 24-hour postoperative mortality may be decreased by about 2-fold, about 3-fold, about 4-fold, about 5-fold, about 10-fold, or more.

In some embodiments, about one month postoperatively, the therapeutically effective amount of the fat emulsion decreases a marker of myocardial injury selected from serum cardiac troponin, serum heart-type fatty acid binding protein, or a combination thereof, by at least 10% at as compared to a control group that did not receive the fat emulsion. For example, the marker may be decreased by about 10%, about 20%, about 30%, about 40%, or about 50%. In another example, the marker may be decreased by about 60%, about 70%, about 80%, about 90%, or about 100%. In still another example, 24-hour postoperative mortality may be decreased by about 2-fold, about 3-fold, about 4-fold, about 5-fold, about 10-fold, or more.

In each of the above embodiments, the decrease may also be expressed as a fold-change, for example, about 2-fold, about 3-fold, about 4-fold, about 5-fold, about 10-fold, or more. The percent decrease or fold-change may also be expressed as a range. For example, the decrease may be between about 10% and about 50%, between about 25% and about 75%, between about 50% and about 100%, between about 75% and about 125%, between about 1-100 fold, about 1-10 fold, about 1-5 fold, about 1-4 fold, about 1-3 fold, or about 1-2 fold. Alternatively, the decrease may be between about 10% and about 30%, between about 20% and about 40%, between about 30% and about 50%, between about 40% and about 60%, between about 50% and about 70%, between about 60% and about 80%, between about 70% and about 90%, or between about 80% and about 100%.

(g) Postoperative Mortality

The present disclosure also provides methods for decreasing postoperative mortality. A "decrease in postoperative mortality" refers to a decrease in a relative risk. In one aspect, the method comprises intravenously administering to a subject, before surgery begins, a therapeutically effective amount of a fat emulsion. Suitable fat emulsions are detailed above in Section (b), and details of their administration are described in Section (c). In an exemplary embodiment, a fat emulsion comprises a combination listed in Table A. In another exemplary embodiment, a fat emulsion consists of a combination listed in Table A. In another exemplary embodiment, a fat emulsion is Intralipid® 10%, Intralipid® 20%, or Intralipid® 30%. Suitable subjects have a mean arterial pressure (MAP) greater than or equal to 66 mmHg at the time of administration, and are further described above in Section (a). In certain embodiments, the subject has a greater risk for intraoperative hypotension. Non-limiting examples of subjects at greater risk for intraoperative hypotension include subjects under general or regional anesthesia that also have: a prior history of intraoperative hypotension, have vasoplegia, have cardiovascular disease, have coronary artery disease, have diabetes, are taking angiotensin converting enzyme inhibitors, are taking angiotensin receptor blockers, and/or have drugs in their bloodstream that cause hemodynamic instability including but not limited to cocaine.

In another aspect, the disclosure provides methods for decreasing postoperative mortality in a subject following intraoperative hypotension. Suitable subjects are described above in in Section (a). The method comprises intravenously administering to the subject a therapeutically effective amount of a fat emulsion after the subject's mean arterial pressure (MAP) is recovered to greater than or equal to 66 mmHg. Suitable fat emulsions are detailed above in in Section (b), and details of their administration are described in Section (c). In an exemplary embodiment, a fat emulsion comprises a combination listed in Table A. In another exemplary embodiment, a fat emulsion consists of a combination listed in Table A. In another exemplary embodiment, a fat emulsion is Intralipid® 10%, Intralipid® 20%, or Intralipid® 30%. The fat emulsion can be administered intraoperatively or postoperatively, preferably during the intraoperative period but after the subject's MAP recovered.

In another aspect, the present disclosure provides methods for decreasing postoperative mortality following general anesthesia. The method comprises intravenously administering to a subject that is not shock, and/or was not in shock, a therapeutically effective amount of a fat emulsion after the subject has received one or more reperfusion therapies to restore the subject's mean arterial pressure (MAP) to 66 mmHg or greater. Suitable subjects are described above in Section (a). Suitable fat emulsions are detailed above in Section (b), and details of their administration are described in Section (c). In an exemplary embodiment, a fat emulsion comprises a combination listed in Table A. In another exemplary embodiment, a fat emulsion consists of a combination listed in Table A. In another exemplary embodiment, a fat emulsion is Intralipid® 10%, Intralipid® 20%, or Intralipid® 30%. The fat emulsion can be administered intraoperatively or postoperatively, preferably during the intraoperative period but after the subject's MAP recovered.

A decrease in postoperative mortality may be seen at one or more times prior to discharge (e.g., about 24 hours postoperatively to discharge), at one or more times following discharge (e.g., discharge to about 12 months postoperatively), or a combination thereof.

For example, in some embodiments, 24-hour postoperative mortality is decreased by at least 10% as compared to a control group that did not receive the fat emulsion. 24-hour postoperative mortality may be decreased by about 10%, about 20%, about 30%, about 40%, or about 50%. In another example, 24-hour postoperative mortality may be decreased by about 60%, about 70%, about 80%, about 90%, or about 100%. In still another example, 24-hour postoperative mortality may be decreased by about 2-fold, about 3-fold, about 4-fold, about 5-fold, about 10-fold, or more.

In other embodiments, 7-day postoperative mortality is decreased by at least 10% as compared to a control group that did not receive the fat emulsion. For example, 7-day postoperative mortality may be decreased by about 10%, about 20%, about 30%, about 40%, or about 50%. In another example, 7-day postoperative mortality may be decreased by about 60%, about 70%, about 80%, about 90%, or about 100%. In still another example, 7-day postoperative mortality may be decreased by about 2-fold, about 3-fold, about 4-fold, about 5-fold, about 10-fold, or more.

In further embodiments, 30-day postoperative mortality is decreased by at least 10% as compared to a control group that did not receive the fat emulsion. For example, 30-day postoperative mortality may be decreased by about 10%, about 20%, about 30%, about 40%, or about 50%. In another example, 30-day postoperative mortality may be decreased by about 60%, about 70%, about 80%, about 90%, or about 100%. In still another example, 30-day postoperative mortality may be decreased by about 2-fold, about 3-fold, about 4-fold, about 5-fold, about 10-fold, or more.

In still other embodiments, 3-month postoperative mortality is decreased by at least 10% as compared to a control group that did not receive the fat emulsion. For example, 3-month postoperative mortality may be decreased by about 10%, about 20%, about 30%, about 40%, or about 50%. In another example, 3-month postoperative mortality may be decreased by about 60%, about 70%, about 80%, about 90%, or about 100%. In still another example, 3-month postoperative mortality may be decreased by about 2-fold, about 3-fold, about 4-fold, about 5-fold, about 10-fold, or more.

In still other embodiments, 6-month postoperative mortality is decreased by at least 10% as compared to a control group that did not receive the fat emulsion. For example, 6-month postoperative mortality may be decreased by about 10%, about 20%, about 30%, about 40%, or about 50%. In another example, 6-month postoperative mortality may be decreased by about 60%, about 70%, about 80%, about 90%, or about 100%. In still another example, 6-month postoperative mortality may be decreased by about 2-fold, about 3-fold, about 4-fold, about 5-fold, about 10-fold, or more.

In still other embodiments, 12-month postoperative mortality is decreased by at least 10% as compared to a control group that did not receive the fat emulsion. For example, 12-month postoperative mortality may be decreased by about 10%, about 20%, about 30%, about 40%, or about 50%. In another example, 12-month postoperative mortality may be decreased by about 60%, about 70%, about 80%, about 90%, or about 100%. In still another example, 12-month postoperative mortality may be decreased by about 2-fold, about 3-fold, about 4-fold, about 5-fold, about 10-fold, or more.

In each of the above embodiments, the percent decrease or fold-change may also be expressed as a range. For example, the decrease may be between about 10% and about 50%, between about 25% and about 75%, between about 50% and about 100%, between about 75% and about 125%, between about 1-100 fold, about 1-10 fold, about 1-5 fold, about 1-4 fold, about 1-3 fold, or about 1-2 fold. Alternatively, the decrease may be between about 10% and about 30%, between about 20% and about 40%, between about 30% and about 50%, between about 40% and about 60%, between about 50% and about 70%, between about 60% and about 80%, between about 70% and about 90%, or between about 80% and about 100%.

What is claimed is:

1. A method for decreasing postoperative myocardial infarction in a subject following intraoperative hypotension, the method comprising intravenously administering to the subject a therapeutically effective amount of a fat emulsion after the subject's mean arterial pressure (MAP) is recovered to greater than or equal to 66 mmHg,
wherein administration of the therapeutically effective amount of the fat emulsion results in at least a 10% decrease in a postoperative myocardial infarction as compared to a control group that did not receive the fat emulsion.

2. The method of claim 1, wherein the decrease is measured about two hours, twelve hours, twenty-four hours, seven days, fourteen days, thirty days, three months, or six months postoperatively.

3. The method of claim 1, wherein the subject's arterial blood flow was reduced but not completely occluded during the period of intraoperative hypotension.

4. The method of claim 1, wherein the intraoperative hypotension occurred for at least about 30 seconds, at least about one minute, at least about five minutes, or at least about ten minutes.

* * * * *